United States Patent
Revol-Cavalier

(10) Patent No.: US 8,354,017 B2
(45) Date of Patent: Jan. 15, 2013

(54) METHOD AND CELL FOR MEASURING THE GLOBAL ION CONCENTRATION OF A BODY FLUID

(75) Inventor: Frederic Revol-Cavalier, Seyssins (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 306 days.

(21) Appl. No.: 12/886,239

(22) Filed: Sep. 20, 2010

(65) Prior Publication Data

US 2011/0079521 A1    Apr. 7, 2011

(30) Foreign Application Priority Data

Oct. 2, 2009    (FR) ...................................... 09 04709

(51) Int. Cl.
*G01N 27/403* (2006.01)
(52) U.S. Cl. ........................ 205/789; 204/416
(58) Field of Classification Search .......... 204/416–420; 205/789, 789.5
See application file for complete search history.

(56) References Cited

U.S. PATENT DOCUMENTS

| | | | |
|---|---|---|---|
| 6,198,953 B1 | 3/2001 | Webster et al. | |
| 6,746,594 B2 * | 6/2004 | Akeson et al. | 205/777.5 |
| 2007/0086927 A1 | 4/2007 | Natarajan et al. | |
| 2009/0201035 A1 | 8/2009 | Kaltenbach et al. | |

FOREIGN PATENT DOCUMENTS

GB    2036977 A    *    7/1980

OTHER PUBLICATIONS

K. Mahabadi et al., "Restrictive dual capacitively coupled contactless conductivity detection for microchip electrophoresis," *Procedia Chemistry*, Elsevier, Proceedings of the Eurosensors XXIII conference, Jan. 9, 2009, pp. 1351-1354, vol. 1, No. 1.
A. Shamsuddin et al., "Continuous monitoring of sweating by electrical conductivity measurement," *Physiological Measurement*, Institute of Physics Publishing, Jan. 8, 1998, pp. 375-382, vol. 19, No. 3.

* cited by examiner

*Primary Examiner* — Alex Noguerola
(74) *Attorney, Agent, or Firm* — Oliff & Berridge, PLC

(57)    ABSTRACT

Method for measuring the global ion concentration of a body fluid that comprises application of a stable DC voltage between first and second electrodes of a cell for measuring the global ion concentration of a body fluid so as to cause electrochemical hydrolysis reactions of the body fluid water to occur at the level of said first and second electrodes, measurement of a hydrolysis current generated by said electrochemical hydrolysis reactions of the water and determination of the global ion concentration of the body fluid by comparison with a previously defined calibration curve. The measuring cell comprises a fluid channel having an internal cross-section smaller than or equal to 1.5 mm.

17 Claims, 12 Drawing Sheets

# METHOD AND CELL FOR MEASURING THE GLOBAL ION CONCENTRATION OF A BODY FLUID

BACKGROUND OF THE INVENTION

The invention relates to a method for measuring the global ion concentration of a body fluid and to a cell for measuring the global ion concentration of a body fluid.

STATE OF THE ART

Conductivity meter measurements are commonly used to determine the global concentration of ions contained in a liquid. This technique finds a large number of applications in the field of chemistry and biochemistry to dose and monitor the progression of the ion concentration of a solution in time. Conductivity measurement is used for example in the environmental field to monitor river water pollution or in the medical field for analysis of physiological solutions and/or body fluids such as a person's sweat.

Conductivity measurements are conventionally made in a conductivity measuring cell comprising at least two electrodes facing one another, immersed in a liquid to be analyzed constituting the electrolyte. A voltage is applied between the two electrodes, generally made from platinum and/or platinized platinum. The ions present in the liquid to be analyzed then close the electric circuit and a current is then measured, the intensity of which current varies according to the conductance of the liquid to be analyzed. In this way, once calibrated, the cell enables the conductivity of the liquid to be measured. The conductivity is proportional to the global ion concentration of the solution, for highly dissociated solutions of sodium or potassium chloride type.

It is known to make conductivity measurements of sweat to diagnose mucoviscidosis in infants from the chlorine concentration in the sweat. The conductivity of the sweat is measured and then converted into NaCl molarity.

Furthermore, the variation of the ionic conductivity or of the electrical resistance of sweat, which is a function of the ion concentration, provides information on the physiological modifications of a person. Dehydration of a sports person or of a soldier can thus be monitored from the variation of the ionic conductivity of his/her sweat.

Measuring devices currently exist that are able to be used for a body fluid collected beforehand on a person. For sweat, the latter is collected for example by means of absorbent membranes in the form of patches and then subsequently analyzed in a laboratory or by the person himself/herself. Absorption of drugs can for example be estimated from such devices.

Embedded measuring devices also exist, located on the person himself/herself, which enable measurement to be made directly on the person in real time and continuously.

For example purposes, the document U.S. Pat. No. 6,198,953 describes a portable device and a method for continuous sweat collection and analysis. The method comprises penetration of a sudorific substance, pilocarpine, into the skin by iontophoresis to stimulate sweat secretion of the sweat glands of the epidermis, followed by measurement of the electrical conductivity of the sweat collected from two electrodes. An analysis circuit tests the conductivity of the sweat flow passing between the two electrodes. These electrodes then produce an electric signal proportional to the ion concentration in response to the current flowing via the sweat.

Conductivity measurement nevertheless imposes application of a low voltage, in general one volt, between the electrodes and voltage scanning.

Under a high DC voltage, the electrodes are indeed the seat of electrochemical reactions and they polarize. The anions and cations present in the ionic solution then migrate to the polarized electrodes and induce an electric field in the opposite direction to the field imposed by the voltage generator. This antagonistic electric field modifies the electrical resistance of the ionic solution and gives rise to the appearance of stray capacitances, which are sources of error on measurement of the global ion concentration. To solve this problem, an AC voltage has to be applied with voltage frequency scanning. Frequency scanning enables the direction of the voltage to be alternated to prevent the migration phenomenon from occurring and to inhibit the electrochemical reactions in the vicinity of the electrodes. The scanning frequency then has to be sufficiently high to prevent these parasitic phenomena. This frequency linked to the nature of the electrolyte is conventionally situated between 10 Hertz and 1000 Hertz. Measurement of the ion concentration by conductivity measurement consequently requires frequency control of the voltage and implementation of a suitable analysis circuit.

Several devices using an AC current have been proposed for measuring conductivity. For example, the publication by Mahabadi K. A. et al., "Restrictive dual capacitively coupled contactless conductivity detection for microchip electrophoresis", Procedia Chemistry, Elsevier, vol. 1. no. 1, Jan. 9, 2009, 1351-1354, the publication by Shamsuddin A. K. et al., "Continuous monitoring of sweating by electrical conductivity measurement", Physiological measurement, Institute of Physics Publishing, Bristol, GB vol. 19, no. 3, Jan. 8, 1998, 375-382 and the documents US-A-20070086927 and US-A-20090201035 can be cited.

The conductivity of an ionic solution further depends on the geometry of the conductivity measuring cell. It is proportional to the surface of the electrodes of the conductivity measuring cell and inversely proportional to the distance between the two electrodes. The volume of the conductivity measuring cell therefore has to be sufficiently large to be able to arrange the electrodes facing one another. In known manner, the minimum volume of a conductivity measuring cell must not be less than 10 ml so as not to affect the quality of the measurements. These size constraints constitute a drawback for miniaturization of the measuring devices and for the use of such conductivity measuring cells in systems carried by persons where the size of the measuring systems constitutes a critical element.

Conductivity measurement devices of the prior art use electrodes, generally made from platinized platinum, to increase their developed surface. The use of such a material requires frequent calibrations due to the variation of the developed surface by the electrodes, for example due to loss of material. In addition, to avoid excessive wear, such electrodes have to be stored in a damp environment.

OBJECT OF THE INVENTION

The object of the invention is to propose a method for measuring the global ion concentration of a body fluid and a measuring cell remedying the shortcomings of the prior art.

In particular, the object of the invention is to propose a measuring method and cell enabling simple and precise quantitative measurement of the global ion concentration of a body fluid, in particular sweat.

It is a further object of the invention to propose a measuring cell that is able to be miniaturized for minimum volume and weight in order to be easily integrated in a measurement system carried by a person and enabling continuous monitoring of the physiological state of a person.

It is a further object of the invention to propose a method for measuring the global ion concentration of a body fluid using such a measuring cell.

According to the invention, this object is achieved by a method and cell for measuring the ion concentration of a body fluid according to the indexed claims.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF PARTICULAR EMBODIMENTS OF THE INVENTION

Figure 1:
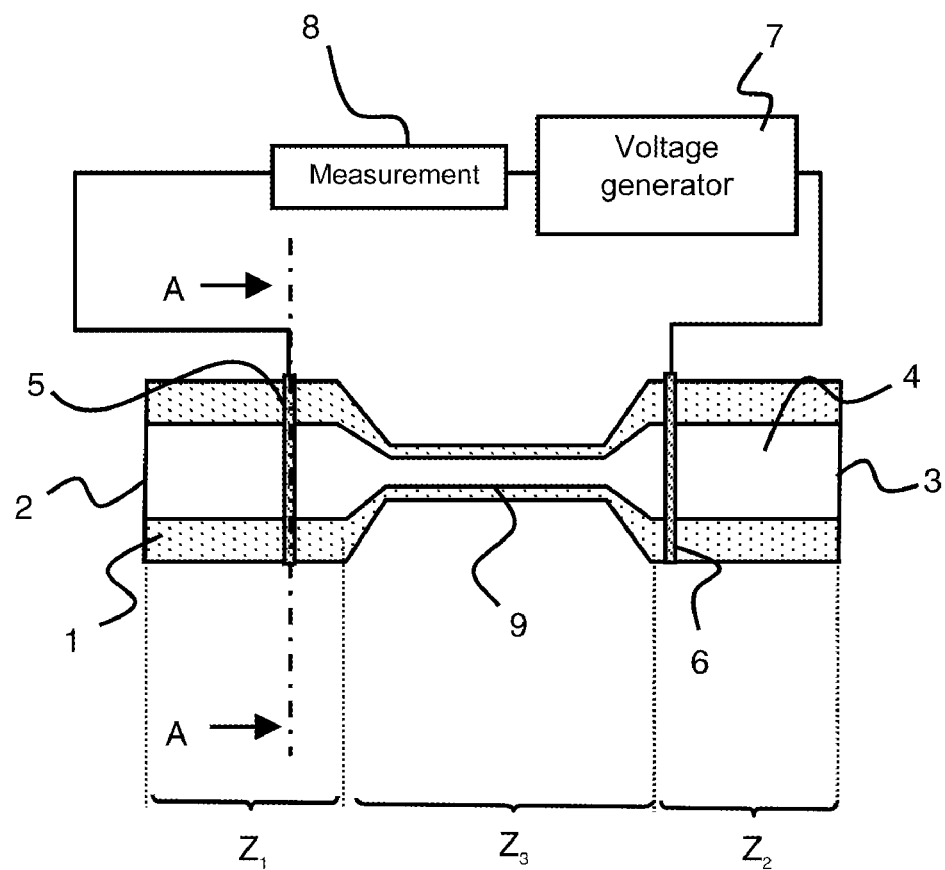
FIG. 1 schematically represents a cross-section of a particular embodiment of a cell for measuring the ion concentration of a body fluid according to the invention.

As represented in FIG. 1, a cell for measuring the global ion concentration of a body fluid comprises a fluid channel 1 with an inlet 2 and outlet 3 for the body fluid. Fluid channel 1 arranges at least one passage 4 for the body fluid enabling the body fluid to flow from inlet 2 to outlet 3.

The measuring cell also comprises first and second electrodes, respectively 5 and 6, connected to a voltage generator 7 and to an electronic measurement circuit 8. Voltage generator 7 and electronic measurement circuit 8 are conventionally connected in series.

Voltage generator 7 can advantageously be a potentiostat or a battery, for example with a voltage of 4.5V.

Voltage generator 7 and electronic measurement circuit 8 are connected in series to enable an current electric to be measured. Electronic measurement circuit 8 can advantageously be an ammeter. Alternatively, electronic measurement circuit 8 can be a measuring device enabling the electron flux collected by the electrodes, respectively 5 and 6, to be determined. In preferred manner, this measuring device 8 is connected to a data processing system, the latter being able to be integrated in electronic measurement circuit 8 in the form of a printed circuit card or an ASIC (Application Specific Integrated Component).

Between the first and second electrodes, respectively 5 and 6, fluid canal 1 has an internal cross-section smaller than or equal to 1.5 mm to limit ionic migration between said electrodes, 5 and 6. The measuring cell advantageously comprises a constriction 9 of the internal cross-section of the fluid channel between first and second electrodes, respectively 5 and 6.

Fluid channel 1 can be a capillary having a continuous internal cross-section. Limitation of the ionic migration between said electrodes, 5 and 6, is induced by the small internal cross-section of the capillary, which is smaller than or equal to about 1.5 mm.

The measuring cell advantageously comprises a constriction 9 of the internal cross-section of the fluid channel between first and second electrodes, respectively 5 and 6. Fluid channel 1 can have an internal cross-section greater than 1.5 mm, and at least one constriction 9 located between first and second electrodes, respectively 5 and 6, reducing the internal cross-section to a value less than or equal to 1.5 mm. Constriction or constrictions 9 are then responsible for limiting ionic migration. This embodiment is preferred as this measuring cell is simple to manufacture and avoids the use of costly small electrodes.

According to a particular embodiment, fluid channel 1 comprises first and second zones, respectively $Z_1$ and $Z_2$, each having a defined internal cross-section, and a third zone $Z_3$ situated between first zone $Z_1$ and second zone $Z_2$, and adjacent to said first and second zones $Z_1$ and $Z_2$. First zone $Z_1$ is connected to inlet 2 and second zone $Z_2$ to outlet 3. The three zones, respectively $Z_1$, $Z_2$ and $Z_3$, are contiguous so that flow of the body fluid in passage 4 can take place from inlet 2 to outlet 3.

Third zone $Z_3$ has a reduced internal cross-section, smaller than the respective internal cross-sections of first and second zones, $Z_1$ and $Z_2$, to limit ionic migration in the body fluid between first and second electrodes, respectively 5 and 6. What is meant by internal cross-section of a zone is the intersection surface between fluid channel 1 and a plane perpendicular to the direction of flow of the fluid on the zone concerned. The intersection surface taken into consideration is that delineated by the inner wall of fluid channel 1. When the internal cross-section varies along the zone concerned, the value taken into account to compare zones $Z_1$, $Z_2$ and $Z_3$ is the smallest internal cross-section value for each zone concerned.

First electrode 5 and second electrode 6 are arranged on passage 4 of fluid channel 1 and respectively situated at the level of first and second zones, respectively $Z_1$ and $Z_2$. First and second electrodes, respectively 5 and 6, are thus arranged on body fluid passage 4 so that at least a part of each electrode 5 and 6 is in contact with the body fluid.

First and second electrodes, respectively 5 and 6, can be either a work electrode and a reference electrode or a work electrode and a counter-electrode.

Figure 2:
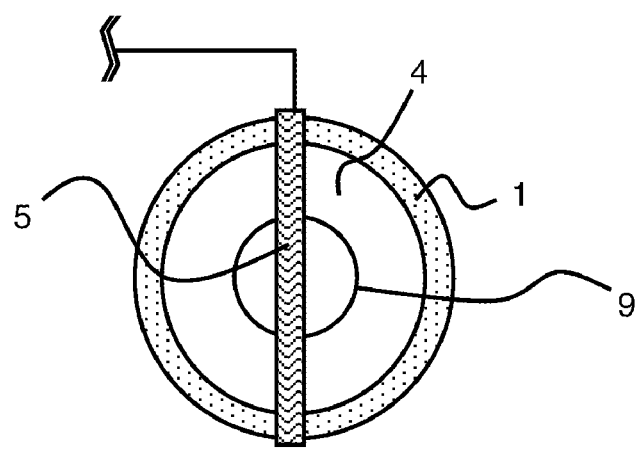
FIG. 2 schematically represents a measuring cell in cross-section along the line AA of FIG. 1.

According to a particular embodiment represented in FIGS. 1 and 2, fluid channel 1 can have a tubular shape. For example, fluid channel 1 can be a flexible or rigid tube made from inert material, preferably a plastic. The inner diameter of the tube at the level of constriction 9 can advantageously vary between 0.1 mm and 1.5 mm. Below 0.1 mm, the current measured by electrodes 5 and 6 is generally too weak due to insufficient ionic migration through constriction 9. Above 1.5 mm, the hydrolysis current generally generates too many bubbles at the level of electrodes, 5 and 6. The bubbles then disturb the measurements and are sources of errors.

First zone $Z_1$ opens out directly on inlet 2 and second zone $Z_2$ opens out directly on outlet 3. Fluid channel 1 can comprises at least one constriction 9 of the tube at the level of third zone $Z_3$. Constriction 9 forms a bottleneck choking passage 4 which makes passage 4 narrower at the level of third zone $Z_3$.

First and second electrodes, respectively 5 and 6, can be carbon or metallic-base electrodes, for example made from steel, gold, aluminum, copper, tin or platinum. Electrodes 5 and 6 are preferably platinum electrodes.

As represented in FIG. 2, first and second electrodes, respectively 5 and 6, are each formed by a wire passing through fluid channel 1 and arranged facing one another. First and second electrodes, respectively 5 and 6, are for example platinum wires having a diameter comprised between 0.2 mm and 1 mm and separated from one another, in the flow direction of the fluid (from left to right in FIG. 1), by a distance varying from a few millimeters to a few centimeters, advantageously by a distance comprised between 2 mm and 20 mm.

Figure 3:
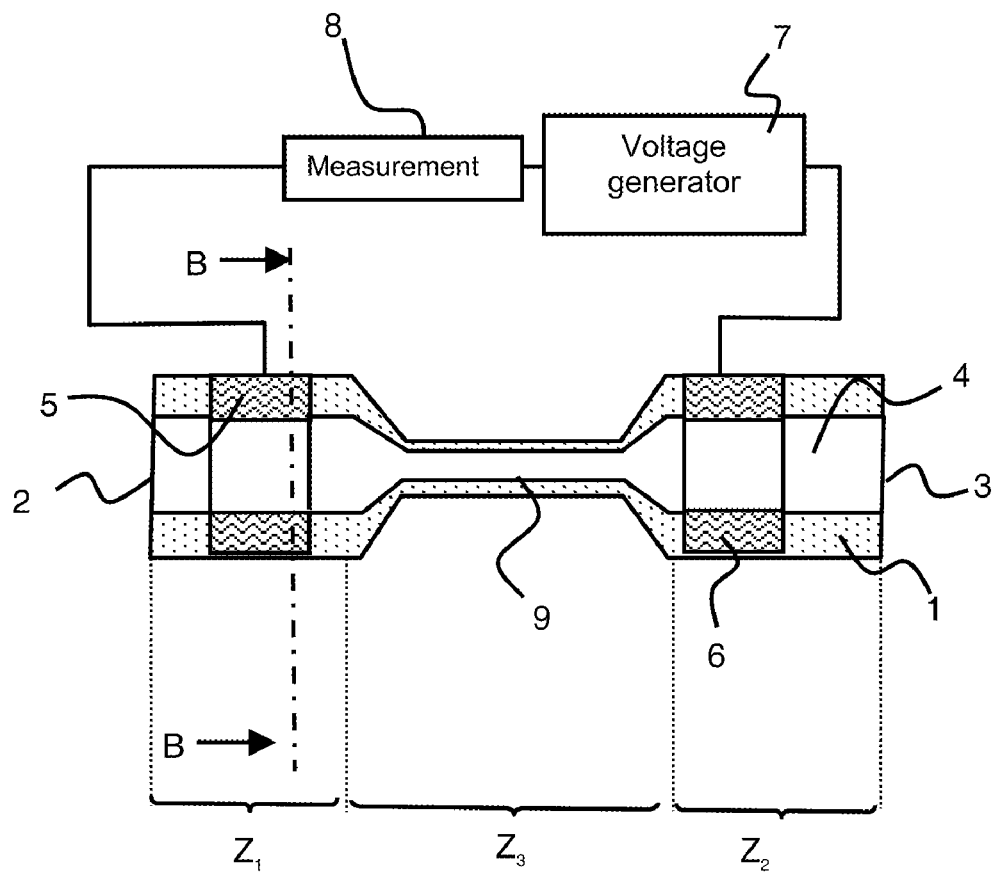
FIGS. 3 and 5 schematically represent cross-sections of alternative embodiments of FIG. 1.
Figure 4:
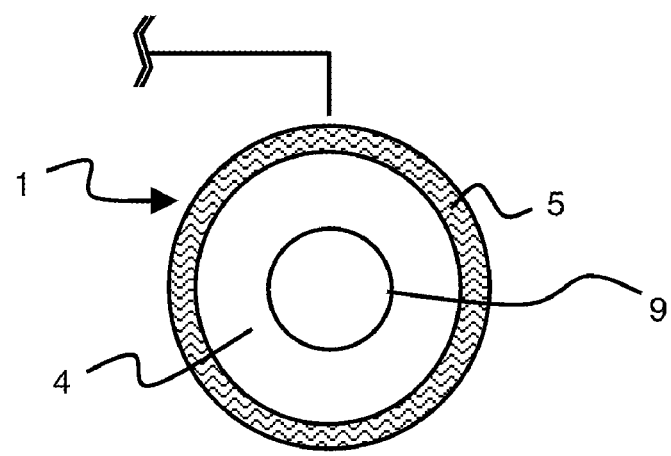
FIGS. 4 and 6 schematically represent a measuring cell in cross-section respectively along the lines BB of FIG. 3 and CC of FIG. 5.

According to an alternative embodiment represented in FIGS. 3 and 4, fluid channel 1 is an annular duct and first and second electrodes, respectively 5 and 6, are also annular and formed in the annular wall of fluid channel 1. First and second electrodes, respectively 5 and 6, are advantageously made from platinum. Alternatively, only the surface of first and second electrodes, respectively 5 and 6, designed to be in contact with the body fluid is covered by a layer of platinum. Deposition of the layer of platinum can be performed by conventional evaporation, sputtering or electrochemical deposition techniques.

For example purposes, the diameter of the annular duct constituting first and second electrodes, respectively 5 and 6, can be comprised between 0.1 mm and 10 mm and the distance between the two electrodes 5 and 6, can be comprised between 1 mm and 200 mm.

Figure 5:
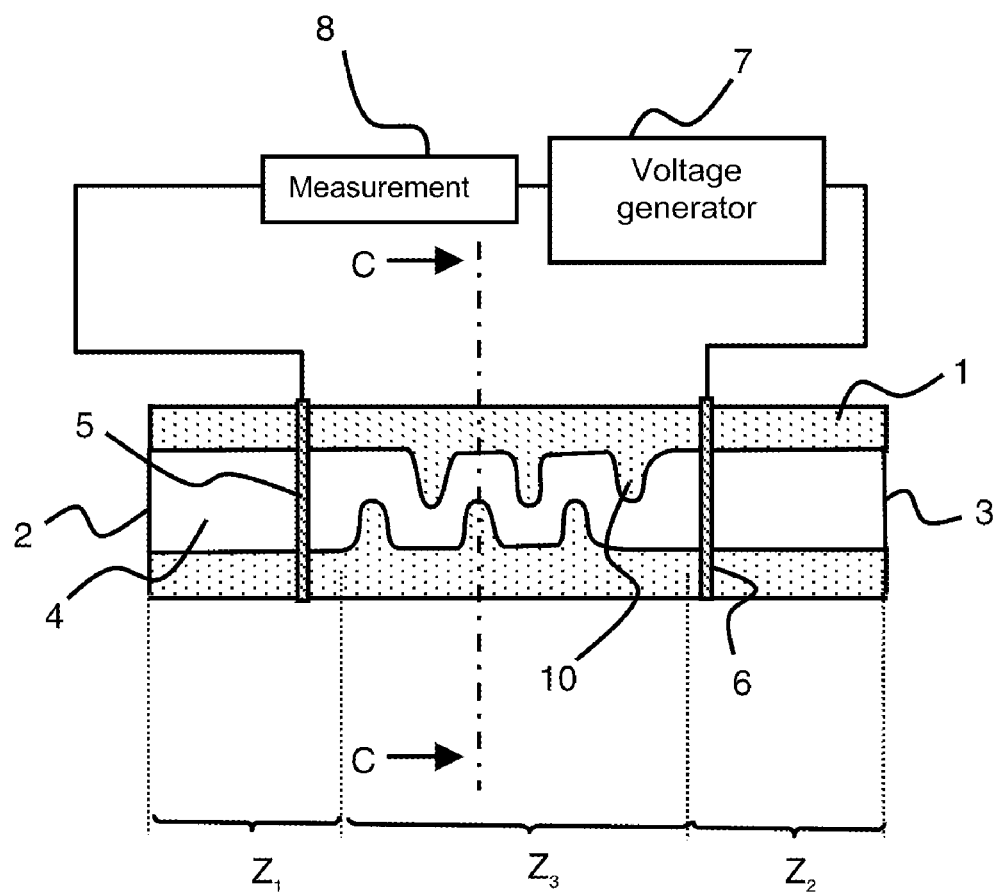
Figure 6:
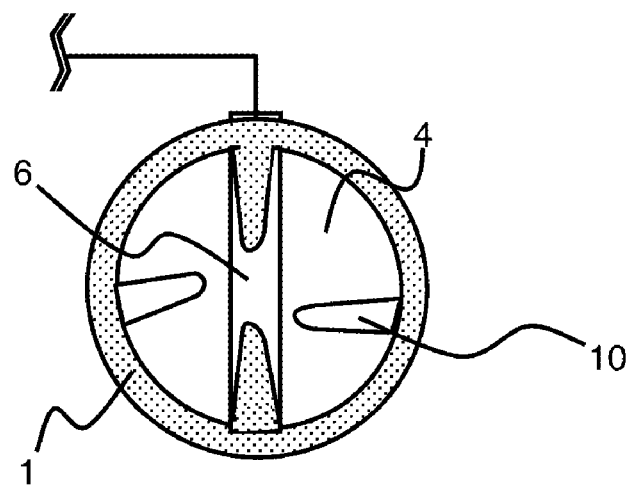

According to another alternative embodiment represented in FIGS. 5 and 6, fluid channel 1 can present protuberances 10 instead of constriction 9 on the surface of inner wall of fluid channel 1, at the level of third zone $Z_3$. Protuberances 10 reduce the internal cross-section of fluid channel 1 at the level of third zone $Z_3$. Protuberances 10 thereby hamper flow of the body fluid and slow down circulation of the body fluid between first and second electrodes, respectively 5 and 6. The extent of limitation of ionic migration in the body fluid between the two electrodes, respectively 5 and 6, will depend on the number of protuberances 10 present in third zone $Z_3$ and on the internal cross-section of this third zone $Z_3$.

Figure 7:
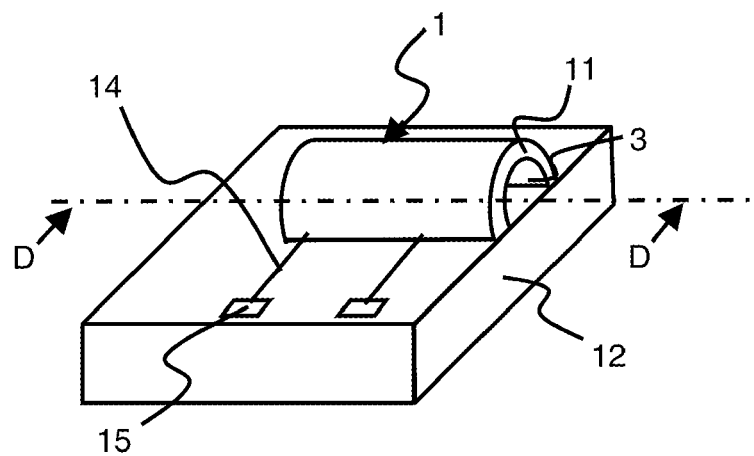
FIG. 7 schematically represents a perspective view of a particular embodiment of a measuring cell according to the invention.

According to another particular embodiment represented in FIG. 7, fluid channel 1 of the measuring cell is delineated by a cover 11 and by at least a part of a support 12, cover 11 being arranged on support 12. Fluid channel 1 consists of a cover 11 at the top part (at the top of FIG. 8) and of at least a part of a flat surface of support 12 at the bottom part (at the bottom of FIG. 8). Fluid channel 1 is for example of semi-cylindrical shape. Passage 4 is consequently delineated by inner wall of cover 11 and the surface of support 12 facing cover 11.

The wall of cover 11 advantageously comprises a larger thickness forming a prominence 13 on passage 4. Prominence 13 forms a reduced internal cross-section and then circumscribes third zone $Z_3$.

Support 12 can be made from a flexible material preferably chosen from polymer materials, textile materials with a base formed by natural or transformed synthetic or vegetal fibers, or cellulose fiber-base materials such as paper.

According to another alternative embodiment, support 12 can be a rigid or semi-rigid material preferably chosen from silicon and glass.

Figure 8:
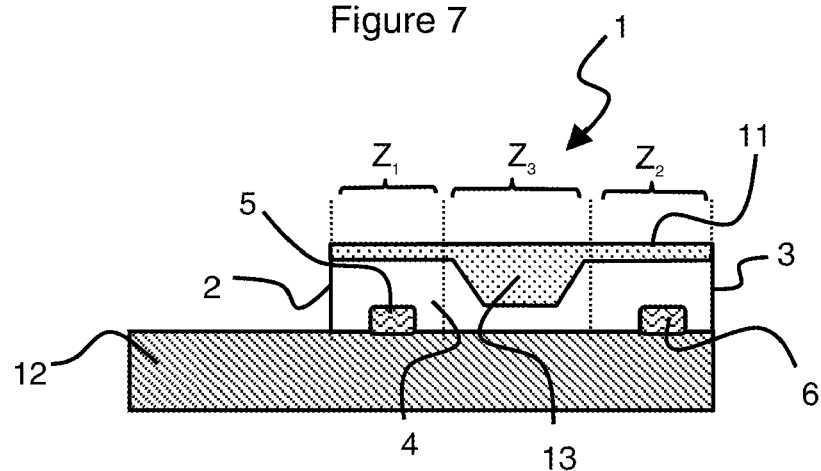
FIG. 8 schematically represents a measuring cell in cross-section along the line DD of FIG. 7.

As represented in FIG. 8, first and second electrodes, respectively 5 and 6, are deposited on one and the same wall of fluid channel 1, advantageously on one and the same wall of support 12. First and second electrodes, respectively 5 and 6, can be deposited on support 12, for example in the form of pads, by conventional deposition techniques used for printed circuits or integrated circuits. First and second electrodes, respectively 5 and 6, formed in this way are coplanar, i.e. they are arranged side by side in the longitudinal direction of passage 4 (left to right in FIG. 8).

First and second electrodes, respectively 5 and 6, are preferably connected to voltage generator 7 and to electronic measurement circuit 8 by connecting means integrated in support 12. The connecting means conventionally comprise connecting wires 14 and an electrical connection system 15. Electrical connection system 15 is preferably arranged at the end of support 12 and is designed to be connected to voltage generator 7 and to electronic measurement circuit 8 of the measuring cell.

Figure 9:
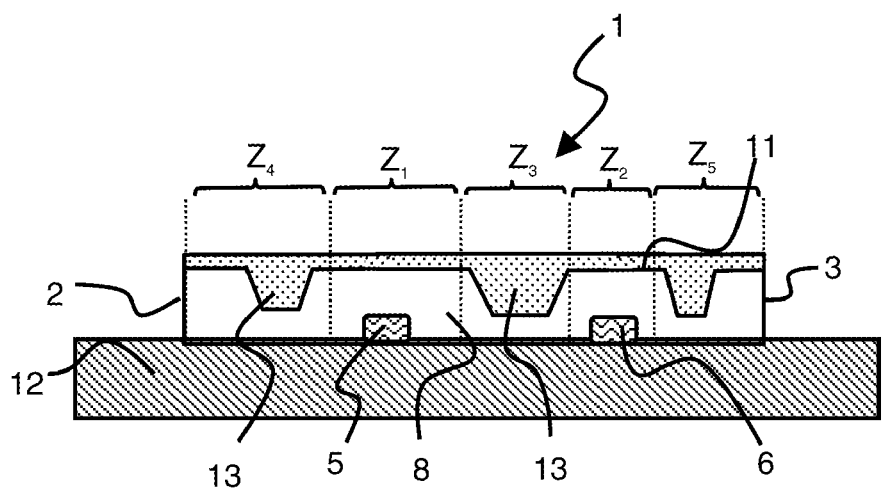
FIG. 9 schematically represents a cross-section of an alternative embodiment of FIG. 8.

According to an alternative embodiment represented in FIG. 9, the measuring cell comprises one or two additional zones $Z_4$ and/or $Z_5$. More particularly, the measuring cell comprises an additional zone $Z_4$ adjacent to first zone $Z_1$ and situated between inlet 2 and first zone $Z_1$ and an additional zone $Z_5$ adjacent to second zone $Z_2$ and situated between second zone $Z_2$ and outlet 3. Each additional zone $Z_4$ and $Z_5$ has a reduced internal cross-section, smaller than the respective internal cross-sections of the first and second zones, respectively $Z_1$ and $Z_2$. The parts of fluid channel 1 respectively corresponding to additional zones $Z_4$ and $Z_5$, can be identical or different. The presence of an additional zone $Z_4$ and/or $Z_5$ in particular enables the flow of body fluid to be regulated for measuring cells designed to be immersed in the body fluid.

Figure 10:
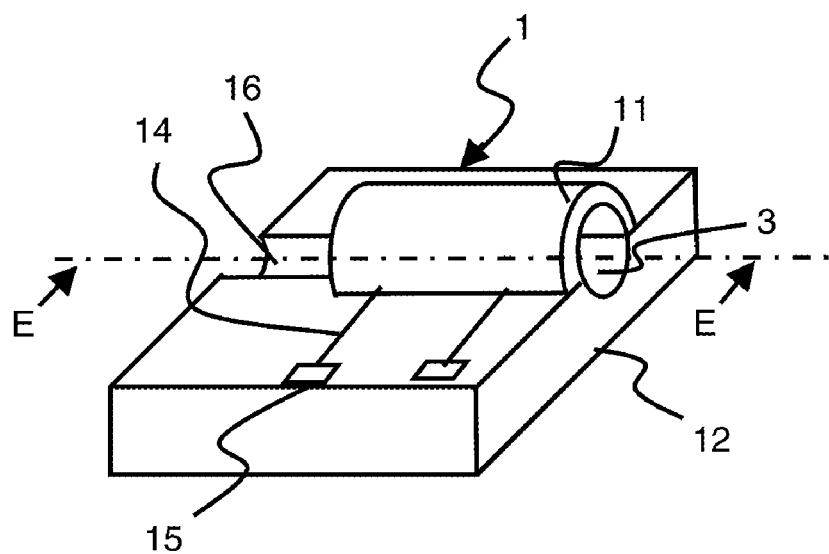
FIGS. 10 and 12 schematically represent perspective views of alternative embodiments of FIG. 7.
Figure 11:
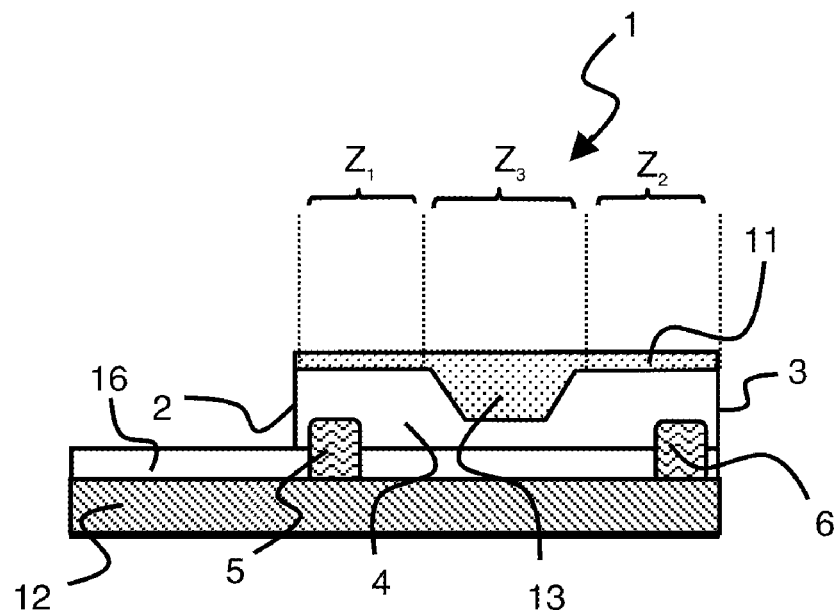
FIGS. 11 and 13 schematically represent a measuring cell in cross-section respectively along the lines EE of FIG. 10 and FF of FIG. 12.

According to an alternative embodiment, support 12 can also comprise means for draining the body fluid to fluid channel 1. As represented in FIGS. 10 and 11, the means for draining consist of at least one groove 16 in support 12. Groove 16 can for example be made continuously from one end of support 12 to the other (left to right in FIGS. 10 and 11). Groove 16 is covered over a part of its length by cover 11. Cover 11 is also arranged facing groove 16 (FIG. 10). First and second electrodes, respectively 5 and 6, are deposited in the bottom of groove 16, respectively in first zone $Z_1$ and in second zone $Z_2$, and are connected to voltage generator 7 and to electronic measurement circuit 8 as described in the foregoing. Means for draining can also be connected to outlet 3 of fluid channel 1 to facilitate removal of the sweat during the measurements. These means for draining can be a mechanical syringe, or a passive fluid pump consisted for example of a channel made from hydrophilic fabric bordered by a channel made from hydrophobic fabric, opening out onto a hydrophilic absorber (not shown).

Figure 12:
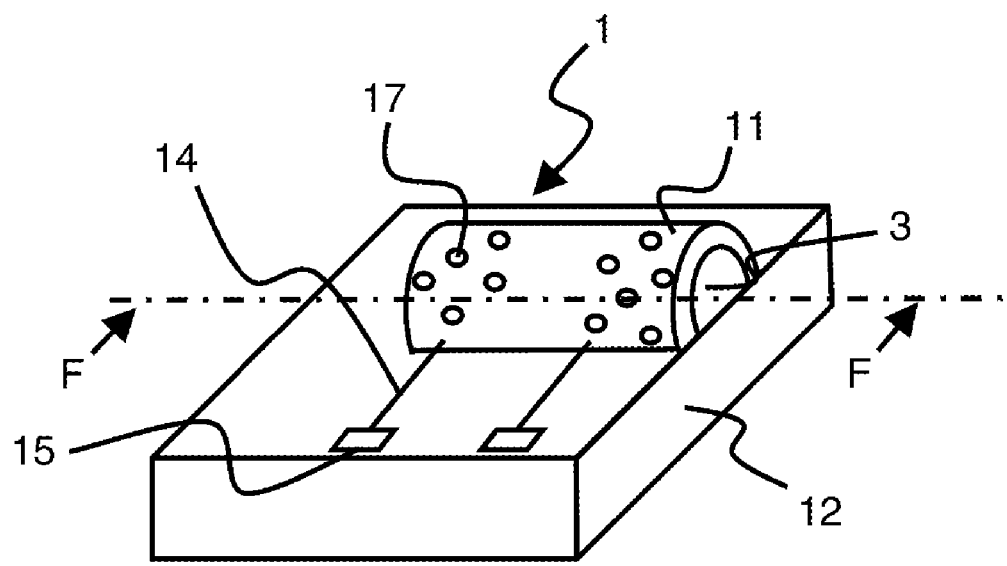
Figure 13:
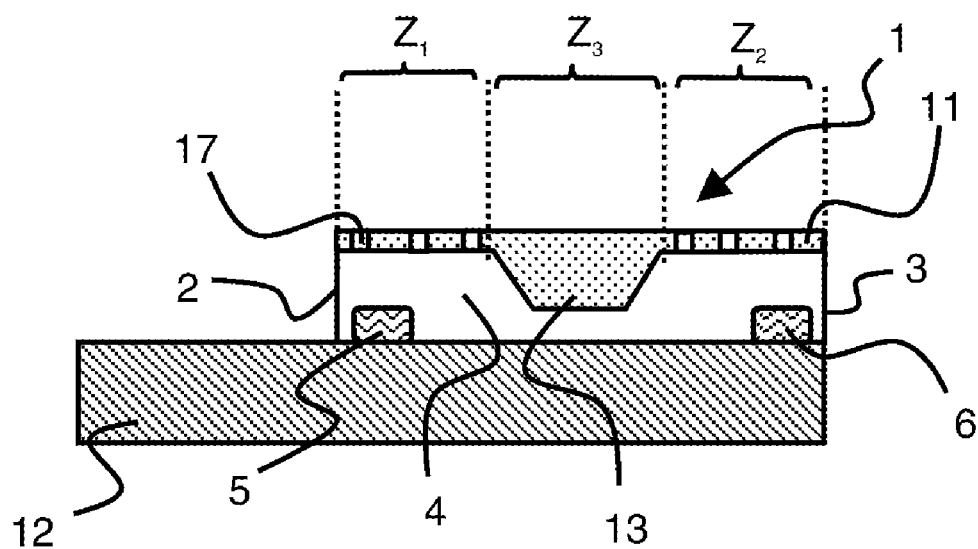

According to another alternative embodiment represented in FIGS. 12 and 13, cover 11 can comprise at least one drain hole 17 passing through the wall of cover 11. Drain hole 17 is situated outside third zone $Z_3$ so as not to reduce the limiting effect of circulation of the ions between first and second electrodes, respectively 5 and 6. Cover 11 advantageously comprises several drain holes 17. Drain hole or holes 17 are designed to foster evacuation of the body fluid. This alternative embodiment is particularly suitable for a measuring cell designed to be immersed in the body fluid.

According to a particular embodiment, the measuring cell advantageously comprises a device for collecting body fluid which feeds body fluid to channel 1. The device for collecting can be an embedded system, for example a sweat pocket arranged directly on a person. The sweat pocket enables a person's sweat to be collected in real time and canalized towards inlet 2 of fluid channel 1. The sweat flows in passage 4 and is then removed via outlet 3. The measuring cell according to this embodiment is particularly suitable for real-time monitoring of variations of the ion concentration for example of a person's sweat. The device for collecting can be connected directly to inlet 2 of fluid channel 1 by a duct (not shown) or connected to support 12.

Figure 14:
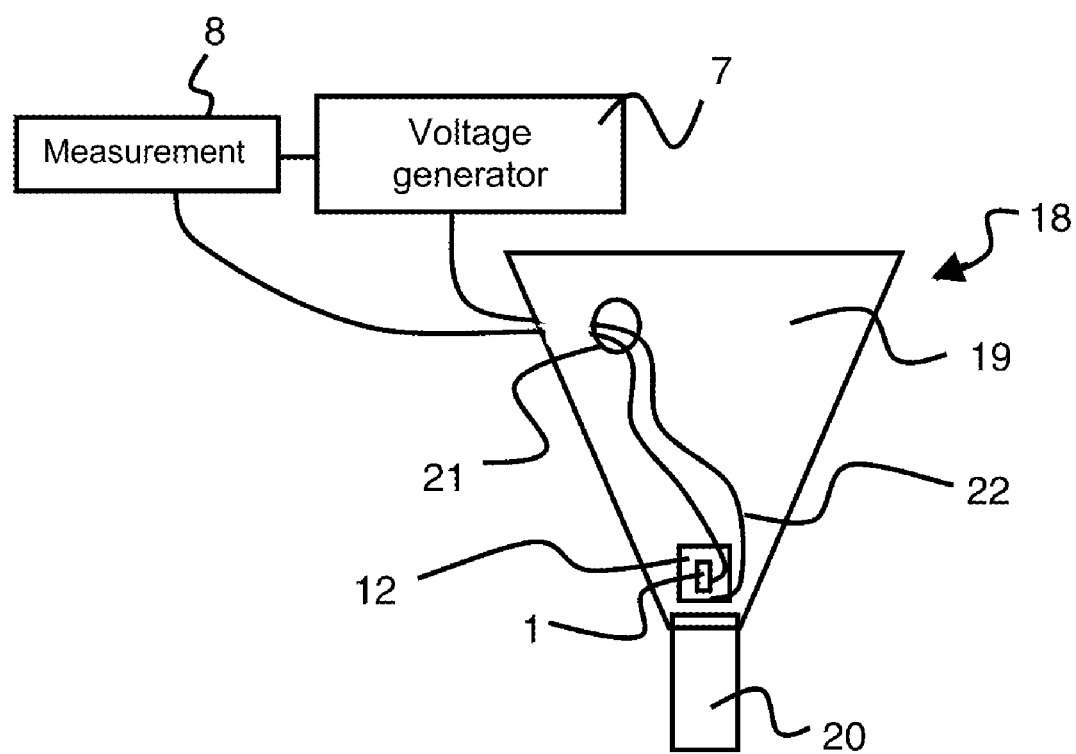
FIG. 14 schematically represents a particular embodiment of a measuring cell according to the invention.

According to a particular embodiment represented in FIG. 14, support 12 of fluid channel 1 forms at least a part of a collecting device 18 consisted for example of a sweat pocket. Collecting device 18 is in the shape of a funnel with a tapered part 19 (at the top of FIG. 14) and a narrow part 20 (at the bottom of FIG. 14). Tapered part 19 acts as receptacle for collecting the sweat given off by the skin and narrow part 20 enables the sweat to be evacuated. Support 12 can advantageously be integrated in the wall of collecting device 18, preferably at the level of tapered bottom part 19 or of narrow top part 20 so that fluid channel 1 can be immersed in the collected sweat.

According to an alternative embodiment that is not represented, support 12 can be stuck or deposited on the inner wall of collecting device 18.

As represented in FIG. 14, an opening 21 can be made for example in tapered top part 19 to enable wires of electric circuit 22 connecting voltage generator 7 and electronic measurement circuit 8 to connection system 15 to run though the wall of collecting device 18.

According to a particular embodiment, a method for measuring the global ion concentration of a body fluid by means of the measuring cell described above comprises application of a stable DC voltage between the first and second electrodes, respectively 5 and 6. The applied voltage is advantageously comprised between 2V and 10V, preferably between 3V and 5V. The voltage is for example applied during a period comprised between 0.1 s and 10 s, preferably between 0.1 s and 4 s.

The body fluid collected is canalized towards fluid channel 1 of the measuring cell, for example by a collecting device 18, and at least partially fills passage 4. The presence of the body fluid between first and second electrodes, respectively 5 and 6, then enables an electrochemical measurement to be made, the body fluid then acting as electrolyte.

Voltage generator 7 and electronic measurement circuit 8 can also be integrated in collecting device 18 in the form of a flexible integrated circuit connected to electrodes 5 or 6. According to an alternative embodiment, electrodes, 5 and 6, are integrated in the flexible integrated circuit. The flexible integrated circuit is then configured so that electrodes 5 and 6 are in contact with the liquid contained in collecting device 18.

Application of a stable DC voltage between first and second electrodes, respectively 5 and 6, cause electrochemical hydrolysis reactions of the body fluid water to occur at the level of said first and second electrodes, 5 and 6. When stable DC voltage is applied between first and second electrodes, respectively 5 and 6, the latter are the seat of the following preponderant electrochemical reactions:

On the anode

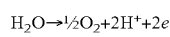

On the cathode

The current generated corresponds to a hydrolysis current of body fluid water. This hydrolysis current depends on several parameters, in particular the surface of the electrodes, the temperature, the applied voltage, and the concentration and diffusion coefficients of the species involved in the electrochemical reactions.

Accumulation of $OH^-$ and $H^+$ ions respectively on the cathode and the anode creates a hydrolysis current which depends on the kinetics of the hydrolysis reactions taking place on first and second electrodes, respectively 5 and 6. Under the action of the electric field, the $OH^-$ and $H^+$ ions acquire a limit speed proportional to the applied field. The ions, cations and anions present in the body fluid act as charge carriers and constitute the carrier salts. The carrier salts convey the charges between first and second electrodes, respectively 5 and 6, thereby closing the circuit. The concentration of carrier salts, generally comprised between $0.005$ mol·l$^{-1}$ and $0.1$ mol·l$^{-1}$, is sufficient to transport the electrons rapidly enough not to limit the kinetics of the electrochemical reactions which take place at the interface between the body fluid and first or second electrode, respectively 5 and 6.

The presence of a fluid channel 1 and of a third zone $Z_3$ of reduced cross-section in the measuring cell enables flow of the body fluid to be controlled and displacement of the ions present in the body fluid, between first and second electrodes, respectively 5 and 6, to be limited. The ion concentration of the body fluid is then the factor limiting the kinetics of the hydrolysis reactions. The hydrolysis current measured is consequently proportional to the ion concentration of the body fluid.

The method comprises measurement of a hydrolysis current generated by said electrochemical hydrolysis reactions of water. Reading of the hydrolysis current induced by application of the voltage between first and second electrodes, respectively 5 and 6, enables the equivalent ion concentration of a body fluid to be determined. The hydrolysis current is therefore advantageously measured by chronoamperometry during application of the voltage. The data can be collected and/or processed during or after measurement of the hydrolysis current. In particular, a mean of the hydrolysis current is calculated from the data collected over the total voltage application time or over a part of this time. For example purposes, a mean of the hydrolysis current is calculated from the hydrolysis current values collected between the first second and the fifth second for a voltage application time of 5 seconds.

The global ion concentration of the body fluid is determined by comparison with a previously defined calibration curve.

The calibration curve is drawn up from reference solutions having known ion concentrations under identical conditions to those of the studied body fluid. The hydrolysis current value or values obtained for the body fluid are plotted on the calibration curve to obtain the equivalent ion concentration of the studied body fluid.

According to an alternative embodiment, the method for measuring comprises an immersion step of the measuring cell in the body fluid before application of the voltage. Once the measuring cell has been immersed in the body fluid, the voltage is applied between first and second electrodes, respectively 5 and 6, and the hydrolysis current measurements are made during application of the voltage.

EXAMPLE 1

Chronoamperometry measurements with a Mica Autolab Type III Potentiostat are made from of a measuring cell according to FIG. 1 having a fluid channel 1 formed by a plastic tube with an internal diameter of 0.6 mm and an external diameter of 1 mm, first and second electrodes, 5 and 6, in the form of platinum wires with a diameter of 0.6 mm separated from one another by 1 cm passing through this tube. The first step consists in drawing up a calibration curve from reference solutions of sodium chloride with a molar concentration of respectively 10 mM, 30 mM, 50 mM, 70 mM and 100 mM. A voltage is applied between first and second platinum electrodes, 5 and 6.

Figure 15:
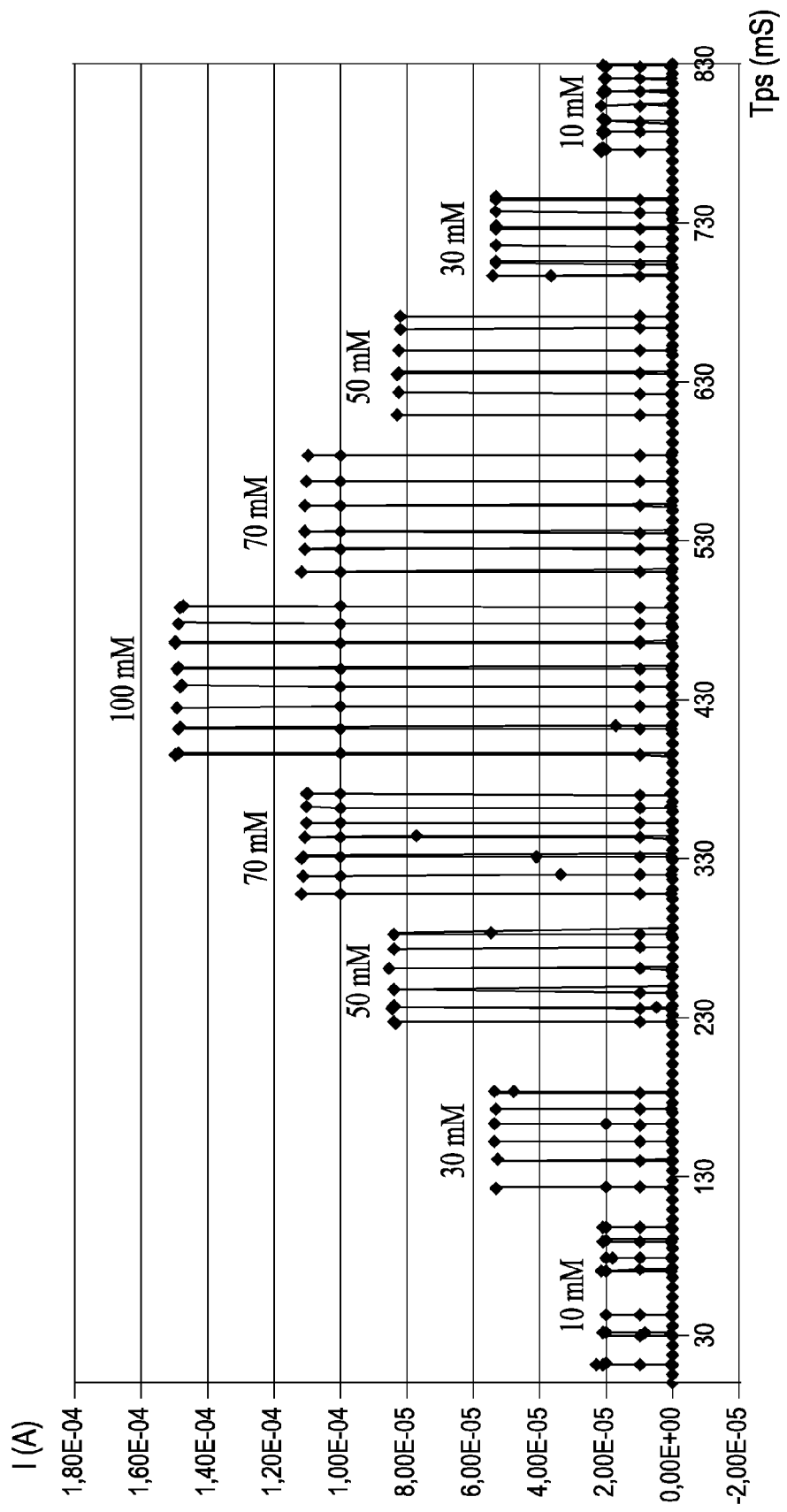
FIGS. 15 and 18 represent the hydrolysis current versus time, measured from a measuring cell according to the invention and from reference solutions.

As represented in FIG. 15, several series of hydrolysis current measurements are made with an interval between each series of measurements according to the following parameters:

Current collection time: 0.5 s
Sampling: 1 measurement every 100 ms

Figure 16:
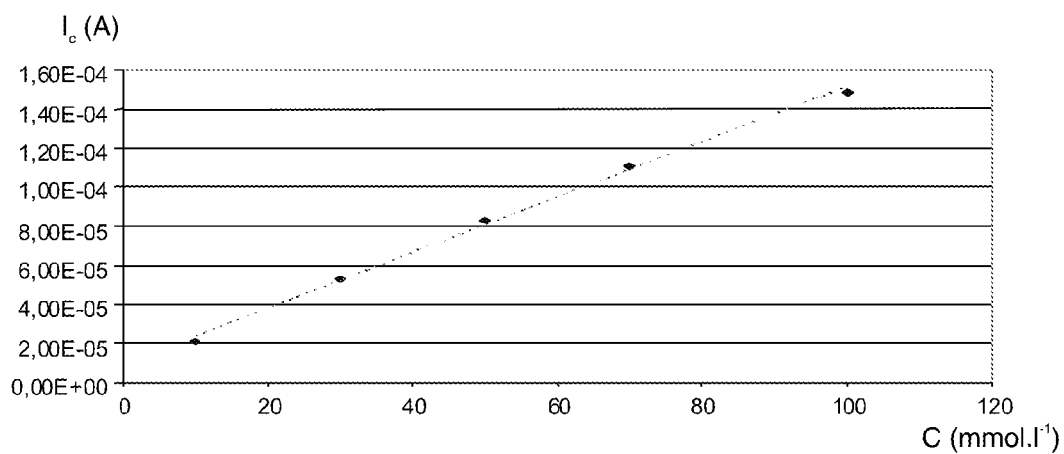
FIG. 16 corresponds to a calibration curve plot representing the mean value of the hydrolysis current collected versus the concentration, obtained from FIG. 15.

The successive collections enable a mean collected current value, called current plateau $I_c$, to be measured, and ensure enhanced reproducibility of the measurements. As illustrated in FIG. 16, for each series of measurements, the current plateau $I_c$ is determined and a straight line is obtained, with a correlation coefficient $R^2$ of 0.997 by plotting the current plateau values versus concentration, $I_c = f(C)$.

Figure 17:
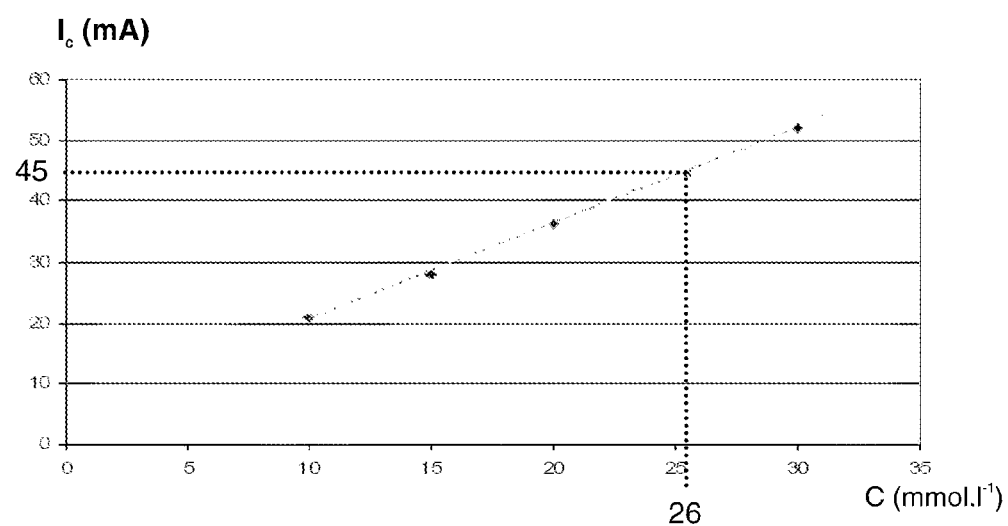
FIGS. 17 and 20 represent a calibration curve obtained respectively from the graph of FIG. 15 and of FIG. 19, with plotting of the mean value of the hydrolysis current collected from a sweat sample.

As illustrated in FIG. 17, a global ion concentration of a sample of sweat collected on a person can be determined from this calibration curve by plotting the hydrolysis current plateau value measured from this sample. For a value $I_c$ of 45 mA, the corresponding global ion concentration value, equivalent to 26 mmol·l$^{-1}$ of NaCl, is read on the calibration curve.

EXAMPLE 2

Figure 18:
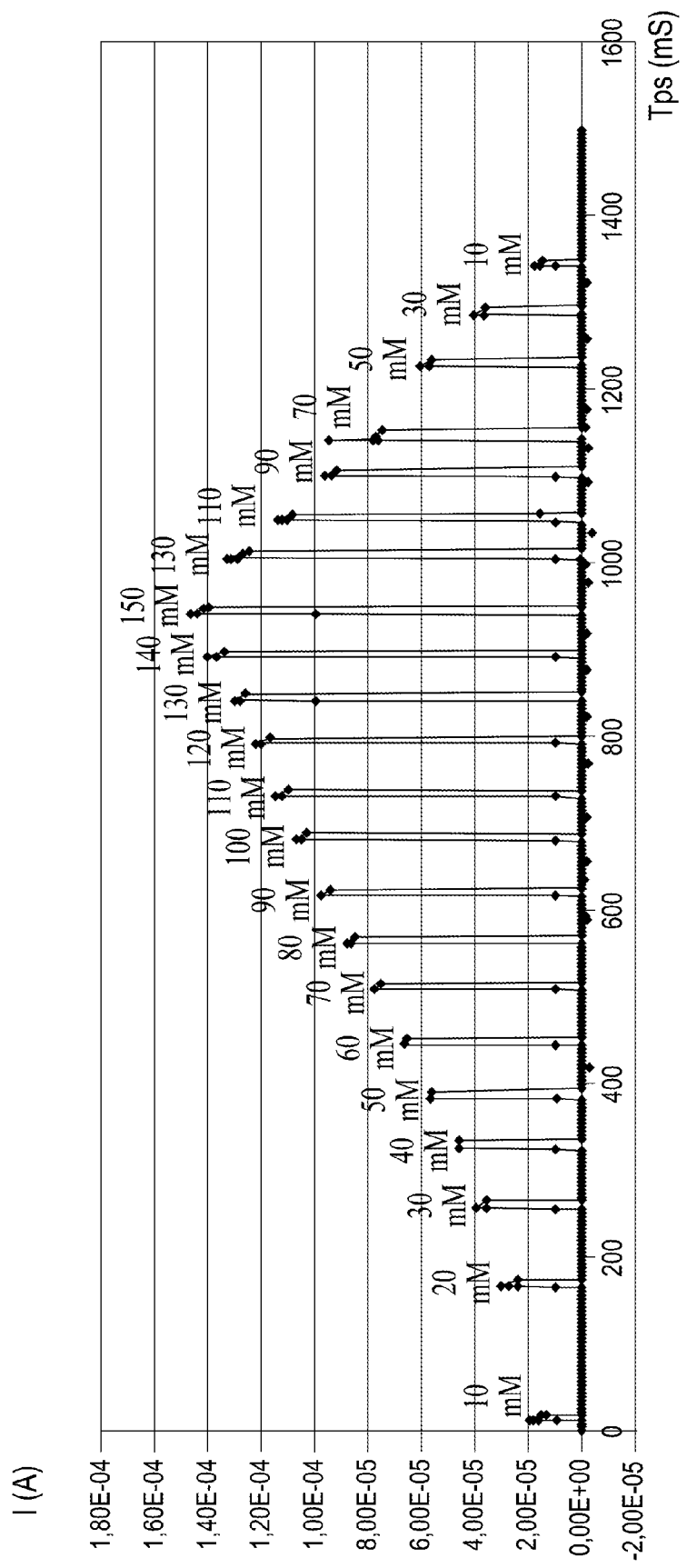
Figure 19:
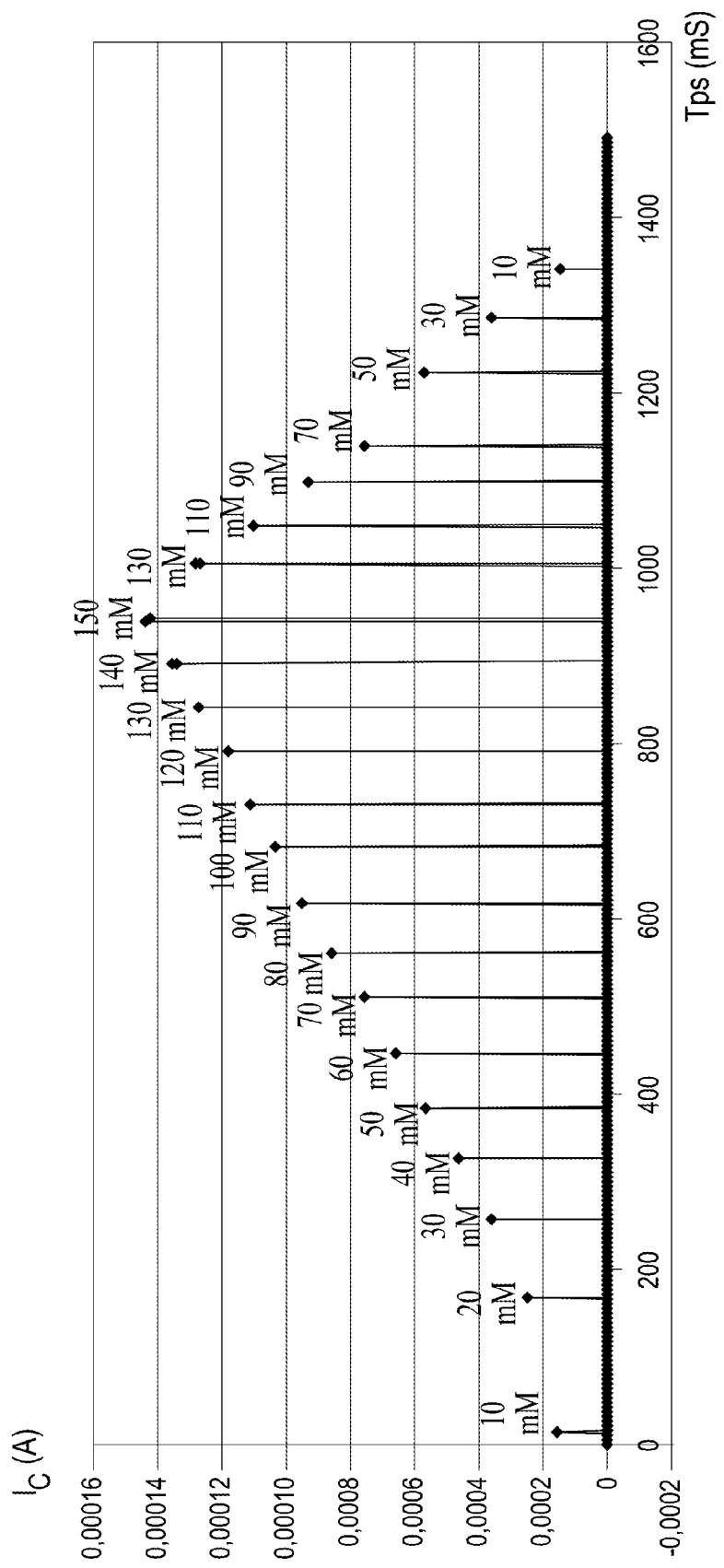
FIG. 19 represents the mean value of the hydrolysis current versus time, obtained from the graph of FIG. 18.
Figure 20:
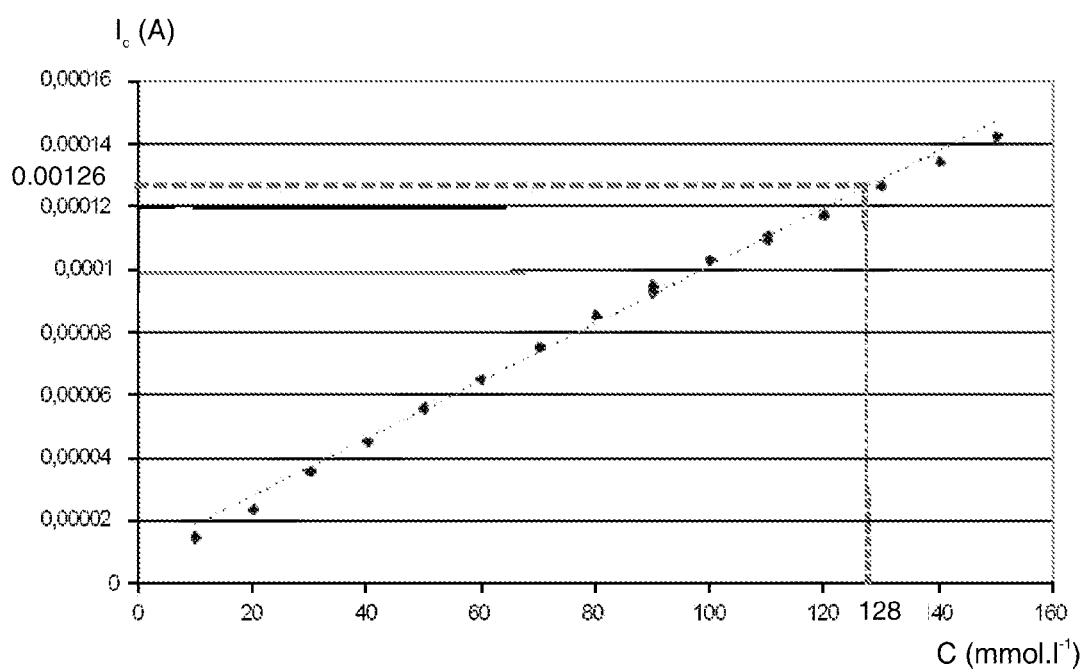

The graphs represented in FIGS. 18 and 19 are obtained from reference solutions of sodium chloride with a molar concentration of respectively 10 mM, 20 mM, 30 mM, 40 mM, 50 mM, 60 mM, 70 mM, 80 mM, 90 mM, 100 mM, 110 mM, 120 mM, 130 mM, 140 mM and 150 mM, under identical conditions to example 1, with the exception of the duration of the current collection time which is longer, being equal to 5 seconds instead of 0.5 seconds. The calibration curve represented in FIG. 20 is achieved from FIG. 19. A straight line is obtained with a correlation coefficient $R^2$ of 0.997. The use of a current collection time of a few seconds prevents bubbles from appearing in the vicinity of electrodes 5 and 6. For a hydrolysis current $I_c$ of 0.00126 A, the global ion concentration is equivalent to 128 mmol·l$^{-1}$ of NaCl.

The method is particularly suited to a body fluid composed mainly of an electrolytic aqueous solution. The body fluid can be a physiological liquid whereof the variation of the ion concentration can indicate pathological states and consequently enable diagnosis of certain diseases such as mucoviscidosis. The body fluids used are preferably aqueous solutions containing highly dissociated ions such as sweat, saliva or urine and having an ion concentration comprised between 0.005 Mol·l$^{-1}$ and 0.1 Mol·l$^{-1}$. The method advantageously enables the ion concentration of the sweat to be measured and an equivalent concentration of sodium chloride (NaCl), a majority carrier salt in sweat, to be obtained.

The method for measuring is simple to set up, inexpensive and enables precise and reliable results to be obtained quickly. Application of a stable DC voltage also presents the advantage of limiting the complexity of the electronics and of circumventing the need for voltage control.

With a concern for miniaturization, measurement cells of small size can be produced by applying microelectronics deposition techniques. The measuring cell according to the invention can easily be integrated in an embedded system such as a sweat pocket fitted on a person. Checking and monitoring of the physiological state of a person can thus be performed continuously.

The invention claimed is:

1. A method for measuring the global ion concentration of a body fluid comprising the following steps:
   application of a stable DC voltage between first and second electrodes of a cell for measuring the global ion concentration of a body fluid so as to cause electrochemical hydrolysis reactions of the body fluid water to occur at the level of said first and second electrodes,
   measurement of a hydrolysis current generated by said electrochemical hydrolysis reactions of water and,
   determination of the global ion concentration of the body fluid by comparison with a previously defined calibration curve,
   said measuring cell comprising a fluid channel arranging at least one passage enabling the body fluid to flow from an inlet to an outlet, said fluid channel having an internal cross-section less than or equal to 1.5 mm between the first and second electrodes arranged on said passage, so that the ion concentration of the body fluid is the factor limiting the kinetics of said electrochemical hydrolysis reactions of the water.

2. The method according to claim 1, wherein measurement of the hydrolysis current is performed by chronoamperometry during application of the DC voltage.

3. The method according to claim 1, wherein the measuring cell comprises a constriction of the internal cross-section of the fluid channel between the first and second electrodes.

4. The method according to claim 1, wherein the voltage applied is comprised between 2V and 10V.

5. The method according to claim 1, comprising an immersion step of the measuring cell in the body fluid before the voltage is applied.

6. The method according to claim 1, wherein the voltage applied is comprised between 3V and 5V.

7. A cell for measuring the global ion concentration of a body fluid which comprises:
   a fluid channel with an inlet and an outlet of the body fluid, and
   first and second electrodes connected to a stable DC voltage generator and to an electronic measurement circuit,
   said fluid channel comprising first and second zones each having a defined internal cross-section and a third zone situated between the first zone and the second zone and adjacent to said first and second zones and arranging at least one passage for the body fluid,
   said third zone having a reduced internal cross-section, smaller than the respective internal cross-sections of said first and second zones, to limit ionic migration between said electrodes in the body fluid,
   said first and second electrodes being arranged on said passage and being respectively situated at the level of the first and second zones.

8. The measuring cell according to claim 7, wherein the fluid channel is delineated by a cover and by at least a part of a support, said cover being arranged on the support.

9. The measuring cell according to claim 8, wherein the support comprises means for draining the body fluid to the fluid channel.

10. The measuring cell according to claim 8, wherein the cover comprises at least one drain hole passing through the wall of the cover and situated outside the third zone.

11. The measuring cell according to claim 8, comprising a body fluid collecting device and wherein the support of fluid channel forms at least a part of said collecting device.

12. The measuring cell according to claim 7, wherein the fluid channel comprises at least one constriction at the level of the third zone making the passage narrower.

13. The measuring cell according to claim 7, wherein the first or second electrodes are both formed by a wire passing through the fluid channel.

14. The measuring cell according to claim 7, wherein the first and second electrodes are formed in the wall of the fluid channel.

15. The measuring cell according to claim 7, wherein the first and second electrodes are deposited on one and the same wall of the fluid channel.

16. The measuring cell according to claim 7, comprising a body fluid collecting device.

17. The measuring cell according to claim 7, comprising an additional zone adjacent to the first zone, situated between the inlet and the first zone, and/or an additional zone adjacent to the second zone and situated between the second zone and the outlet, each additional zone having a reduced internal cross-section, smaller than the respective internal cross-sections of said first and second zones.

* * * * *